United States Patent
Bara

(10) Patent No.: US 6,548,050 B1
(45) Date of Patent: Apr. 15, 2003

(54) MAKE-UP OR CARE COMPOSITION CONTAINING A CROSSLINKED POLYORGANOSILOXANE CONTAINING AN OXYALKYLENATED GROUP

(75) Inventor: Isabelle Bara, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/538,495

(22) Filed: Mar. 30, 2000

(30) Foreign Application Priority Data

Mar. 30, 1999 (FR) .......................................... 99 03967

(51) Int. Cl.⁷ .............................................. A61K 7/025
(52) U.S. Cl. ........................... 424/64; 424/401; 424/59; 424/76.1
(58) Field of Search ........................... 424/401, 64, 59, 424/76.1

(56) References Cited

U.S. PATENT DOCUMENTS

| | | | |
|---|---|---|---|
| 5,387,417 A | | 2/1995 | Rentsch ...................... 424/401 |
| 5,412,004 A | * | 5/1995 | Tachibana et al. ............. 524/27 |
| 6,258,345 B1 | * | 7/2001 | Rouquet et al. .............. 424/64 |

FOREIGN PATENT DOCUMENTS

EP           0 790 055 A1    8/1997

\* cited by examiner

Primary Examiner—Michael G. Hartley
Assistant Examiner—Konata M. George
(74) Attorney, Agent, or Firm—Oblon, Spivak, McClelland, Maier & Neustadt, P.C.

(57) ABSTRACT

The present invention provides a dermatologic or cosmetic composition, including a liquid fatty phase, and, as surfactant and thickener for the liquid fatty phase, particles of a crosslinked elastomeric solid polyorganosiloxane containing at least one oxyalkylenated group. Another embodiment of the invention relates to methods of using particles of a crosslinked elastomeric solid polyorganosiloxane containing at least one oxyethylenated group. The present invention is especially suitable for a care or make-up composition for human skin and lips, and overcomes the various drawbacks in known compositions. In particular, the present invention provides a composition for human skin and lips that results in a film that does not transfer; that has better cosmetic properties, freshness and matte-effect properties; and that is desirably longer-lasting than conventional "transfer-resistant" products, in particular the properties of slipperiness, of not feeling taut and of not drying out the lips, of having good staying power over time, particularly with respect to the color (no color change over time) and of not migrating, in particular into the folds of the skin. The invention applies not only to make-up products for human lips and skin, but also to care and/or treatment products for human lips and skin. The composition of the invention can also be applied to the scalp.

43 Claims, No Drawings

MAKE-UP OR CARE COMPOSITION CONTAINING A CROSSLINKED POLYORGANOSILOXANE CONTAINING AN OXYALKYLENATED GROUP

BACKGROUND OF THE INVENTION

1. Field of the Invention

The present invention relates to a care and/or make-up composition for human skin and/or lips which has both long-lasting matte-effect properties and freshness properties. This composition is, in particular, a lipstick, an eyeliner, a face powder, an eyeshadow or a foundation, or alternatively an antisun product, a deodorant or a treating shampoo. It is preferably in the form of an anhydrous gel, a more or less thick lotion or cream, or a product cast as a stick or in a dish.

The invention also relates to the use of particles of a specific polyorganosiloxane in order to give the skin or the lips a matte effect and/or to camouflage imperfections thereof.

2. Discussion of the Background

Conventional lipstick and foundation compositions generally contain fatty substances such as oils, pasty compounds and waxes, as well as a particulate phase generally composed of fillers and pigments. The fillers generally serve to modify the texture of the composition, as well as to give a matte effect to a film of the composition that is deposited on the skin and/or the lips, while the pigments generally serve to give color to the composition.

The matte effect is particularly desired for users with combination skin or greasy skin, as well as in hot and/or humid climates. The matte-effect fillers used are usually absorbent fillers; in particular, fillers which absorb sebum and the excess oil introduced by the composition, such as talc, silica, kaolin or Nylon powder; or else fillers which have optical properties of scattering light, these properties being known as the "soft focus" effect. These fillers, however, have a tendency to dry out the skin and to emphasis the skin relief, in particular the wrinkles and pores, thus accentuating the local imperfections. In addition, absorbent fillers give the skin a somewhat unnatural powdery appearance, and they have a matte effect which is not long-lasting.

Matte-effect polymers, such as crosslinked silicone polymers known under the commercial references KSG (KSG 6, 16, 17 and 18) from the company Shin Etsu, Trefils from the company Dow Corning or Gransils from the company Grand Industrie, have been used more recently (see in particular EP-A-790 055).

The drawback of these commercial products is that they give an oily, greasy effect, without giving a fresh effect, thereby making them unsuitable or difficult to use in a hot and/or humid environment and/or for users with greasy skin. Furthermore, these commercial products, even those free of silicone oil (Trefils 505 C from Dow Corning, for example), are difficult to disperse in an aqueous medium. These products are presented as "water-insoluble" elastomeric silicone polymers (see in particular EP-A-0 855 178 from Kao).

These polymers, which are difficult to incorporate into an aqueous phase, are entirely water-repellent. On account of their high incompatibility with water and in particular with sweat, these polymers do not absorb sweat, which even has a tendency to "pearl" at the surface of the skin during perspiration. The matte-effect power of these polymers thus has a tendency to fade out over time. Furthermore, compositions that contain these polymers, such as water-in-oil or oil-in-water emulsion compositions, become destabilized over time.

Emulsions containing this type of polymer have recently been designed (cf. U.S. Pat. No. 5,421,004 from Kose and U.S. Pat. No. 5,599,533 from Estee Lauder) in order to improve their cosmetic properties. Although these emulsions introduce less grease and more freshness than anhydrous products, they lose the matte-effect property initially provided by the crosslinked silicone polymers.

Although there are crosslinked organosiloxane-type compounds that disperse in aqueous media, such as, for example, the compounds of the type, KSG 20 or KSG 21 sold by the company Shin Etsu, and whose specific chemical structure (cf. U.S. Pat. No. 5,236,986 from Shin Etsu) is responsible for this dispersion in aqueous medium (presence of polar groups giving them surfactant properties), these compounds, unlike those of the composition of the invention, provide no particular matte effect, and they are incapable of emulsifying large amounts of water (i.e. up to 70% by weight of water).

There is thus a need for a matte-effect composition, which is stable over time, whose properties on the skin persist over time, and which simultaneously provides a fresh sensation.

Moreover, when the known foundation and/or lipstick compositions are applied to the skin or the lips, they have the drawback of transferring, i.e. of becoming at least partly deposited, or by leaving marks, on certain supports with which they may come into contact, and in particular a glass, a cup, a cigarette, an item of clothing or the skin. This results in mediocre persistence of the film applied to the skin or the lips, making it necessary to freshen the application of the foundation or lipstick composition regularly. The appearance of these unacceptable marks, in particular on shirt collars, can put certain women off using this type of make-up.

Cosmeticians have been interested for several years in "transfer-resistant" lipstick and foundation compositions. Thus, the company Shiseido has envisaged, in its application JP-A-61-65809, "transfer-resistant" lipstick.compositions containing from 1 to 70% by weight of a siloxysilicate resin (with a three-dimensional network) having pendent alkyl chains of 1 to 6 carbon atoms or pendent phenyl chains, from 10 to 98% by weight of a volatile silicone oil containing a cyclic silicone chain, and pulverulent fillers. Similarly, the company Noevier has described, in JP-A-62-61911, "transfer-resistant" lipstick, eyeliner and foundation compositions containing one or more volatile silicones combined with one or more hydrocarbon-based waxes.

Although these compositions are entirely satisfactory as regards the "transfer resistance" property, they have the drawback of leaving on the skin, after the silicone oils have evaporated, a film which becomes uncomfortable over time (sensation of dryness and tautness), which puts a certain number of women off this type of make-up product. To make this type of composition more comfortable to wear, non-volatile oils could be added, but in this case the "transfer-resistance" efficacy would be lost.

More recently, the company Revlon has envisaged, in its application EP-A-602 905, "transfer-resistant" lipsticks containing a cyclic or linear volatile silicone containing pendent methyl chains and a silicone resin containing a pendent esterified chain containing from 12 to 18 carbon atoms. The film of lipstick that remains on the lips after the volatile silicone has evaporated again has the drawback of not feeling comfortable when applied and in particular of being too dry. The above company has also envisaged, in its application EP-A-709 083, "transfer-resistant" foundations containing a volatile silicone combined with a siloxysilicate resin. These foundations again have the drawback of being relatively uncomfortable and dry over time.

In addition, when the foundation or lipstick compositions, in particular the pigments in these compositions, are applied to the skin or the lips, they have a tendency to migrate over time, i.e., to travel inside the wrinkles and fine lines in the skin which surround the lips and the eyes, and to run beyond the outline of the lips, outside the initial line, resulting in an unaesthetic effect. The appearance of these marks has a tendency to put certain women off using this type of make-up.

SUMMARY OF THE INVENTION

Accordingly, one object of the present invention is to provide a care or make-up composition for human skin and lips, which makes it possible to overcome the various drawbacks mentioned above.

Another object of the present invention is to provide a composition for human skin and lips that results in a film that does not transfer.

Another object of the present invention is to provide a composition for human skin and lips that has better cosmetic properties than the "transfer-resistant" products of the prior art, in particular the properties of slipperiness, of not feeling taut and of not drying out the lips.

Another object of the present invention is to provide a composition for human skin and lips having freshness and matte-effect properties that are better than those of the matte-effect products of the prior art.

Another object of the present invention is to provide a composition for human skin and lips having properties that are desirably long-lasting.

Another object of the present invention is to provide a composition for human skin and lips having properties of good staying power over time, in particular of the color (no color change over time) and of not migrating, in particular in the folds of the skin.

The invention applies not only to make-up products for human lips and skin, but also to care and/or treatment products for human lips and skin. The composition of the invention can also be applied to the scalp.

These and other objects of the invention are attained with the present invention, the first embodiment of which provides a dermatologic or cosmetic composition, including:
 a liquid fatty phase, and
 as surfactant and thickener for said liquid fatty phase, particles of a crosslinked elastomeric solid polyorganosiloxane containing at least one oxyalkylenated group.

Another embodiment of the invention provides a method selected from the group including increasing the matte effect of a composition, increasing the staying power of a composition, increasing the resistance of a composition to sebum, reducing the transfer of a composition, reducing the migration of a composition, thickening a liquid fatty phase of a composition, manufacturing a cosmetic composition, manufacturing a composition intended for treating or caring for the skin or the lips, manufacturing a make-up or care composition, and a combination thereof, which includes introducing into the composition particles of a crosslinked elastomeric solid polyorganosiloxane containing at least one oxyethylenated group.

Another embodiment of the invention provides a method selected from the group including imparting a matte effect to the skin or lips or keratin, camouflaging an imperfection of the skin or lips or keratin, caring for or treating the skin or lips or keratin, and a combination thereof, which includes applying to the skin or lips or keratin particles of a crosslinked elastomeric solid polyorganosiloxane containing at least one oxyalkylene group.

DETAILED DESCRIPTION OF THE PREFERRED EMBODIMENTS

A more complete appreciation of the invention and many of the attendant advantages thereof will be readily obtained as the same becomes better understood by reference to the following detailed description of the preferred embodiments of the invention, wherein:

One preferred embodiment of the invention provides a matte-effect make-up or care composition for keratin substances, containing a liquid fatty phase, characterized in that it also contains, as surfactant and thickener for the said fatty phase, particles of a crosslinked elastomeric solid polyorganosiloxane containing at least one oxyalkylenated group.

Another preferred embodiment of the present invention relates to the use of particles of crosslinked elastomeric solid polyorganosiloxane including at least one oxyalkylenated group, and more preferably an oxyethylenated group, in a care or make-up composition.

Another preferred embodiment of the present invention relates to the use of particles of crosslinked elastomeric solid polyorganosiloxane including at least one oxyalkylenated group, and more preferably an oxyethylenated group, for the manufacture of a care or make-up composition.

Another preferred embodiment of the present invention relates to the use of particles of crosslinked elastomeric solid polyorganosiloxane including at least one oxyalkylenated group, and more preferably an oxyethylenated group, to give a matte effect to the skin or the lips and/or to camouflage imperfections of the skin and/or the lips.

Preferably, the composition of the invention is in the form of an aqueous phase dispersed in a liquid fatty phase.

The term "imperfection" means any skin defect such as the microrelief (pores, wrinkles, fine lines), marks and blackheads, and blood capillaries.

The term "elastomeric" means a supple, deformable material which has viscoelastic properties and in particular the consistency of a sponge or a supple sphere. Its modulus of elasticity is such that this material withstands deformation and has a limited capacity for stretching and for contraction. This material is capable of regaining its original shape after it has been stretched. This elastomer is formed from high molecular weight polymer chains whose mobility is limited by a uniform network of crosslinking points.

The polyorganosiloxanes in the composition of the invention contain one or more oxyalkylenated groups and in particular oxyethylenated (OE) groups, for example from 1 to 40 oxyalkylenated units and preferably from 1 to 20 and better still from 12 to 20, which can form polyoxyalkylene chains, and in particular polyoxyethylene chains. These groups can be pendent, at the chain end or intended to link two parts of the silicone structure. The number of silicons bearing these groups is preferably from 1 to 10 and better still from 1 to 6.

Although the invention preferably relates to polyorganosiloxanes containing (an) oxyethylenated group(s) (i.e., most preferably containing only oxyethylenated groups as oxyalkylenated groups), it can also relate to polyorganosiloxanes containing (an) oxypropylenated group(s), (i.e. containing only oxypropylenated groups as oxyalkylenated groups). The polyorganosiloxanes can also contain both one or more 1 to 20 oxyethylenated (OE) group(s), for example, and one or more 0 to 20 oxypropylenated (OP) group(s), for example; these polyorganosiloxanes are also known as polyorganosiloxanes containing (an) alkylethoxy-propylenated group(s). Preferably, the number of oxyethylenated groups is greater than the number of oxypropylenated groups.

Moreover, the silicone structure forming the polymeric skeleton of the polyorganosiloxane is preferably a polymethylsiloxane (PDMS) structure in which some of the methyl groups are optionally substituted with $C_2$ to $C_{30}$ and preferably $C_8$ to $C_{24}$ and better still $C_{10}$ to $C_{20}$ alkyl groups, or phenyl groups, either at the chain end or pendent.

Moreover, the polyorganosiloxane containing (an) oxyalkylenated group(s) can contain one or more silicone skeleton(s) linked together via one or more oxyalkylenated and preferably oxyethylenated groups as defined above or by one or more alkylenated groups, the number of alkylenated groups ranging from 1 to 20 and preferably from 1 to 10. Preferably, it contains at least two polymeric skeletons linked together.

Preferably, the silicone skeleton(s) of the elastomeric polyorganosiloxanes in the composition according to the invention contain from 26 to 80 silicon atoms.

According to the invention, the polyorganosiloxane particles serve as emulsifier of an aqueous phase in a liquid fatty phase.

The elastomeric polyorganosiloxanes in the composition of the invention have the noteworthy power of thickening a liquid fatty phase and of emulsifying a liquid fatty phase in an aqueous phase, and vice-versa; they swell in the liquid fatty phase. They do not dry out the skin and they provide good cosmetic properties, in particular softness, freshness, a matte effect, they are non-greasy, and they do not transfer. These novel elastomers give compositions, which feel comfortable when applied, spread well and feel soft and non-sticky. These cosmetic properties are believed to be due firstly to the texture of the polyorganosiloxanes and secondly to their properties, which are comparable to those of microsponges trapping the oily media, and in particular those of the composition and those secreted by the skin.

These polyorganosiloxanes containing (an) oxyalkylenated and in particular oxyethylenated group(s) are especially suited for imparting the matte-effect property of the compositions according to the invention on the skin. Preferably, the composition is free of matte-effect filler. The composition of the invention can be in the form of a paste, a solid or a more or less fluid cream. It can be an oil-in-water or water-in-oil emulsion which is more or less fluid, a solid or soft anhydrous gel, or a multiple emulsion and in particular a water-in-oil-in-water or oil-in-water-in-oil emulsion. This composition can have the appearance of a lotion, a gel, a cream or a cast product and can even be in the form of an aerosol.

Preferably, the composition of the invention is a simple or multiple emulsion and is free of surfactant. Preferably, this composition contains a large amount of water, greater than 70% of the total weight of the composition. More preferably, the composition contains greater than 75% water, and most preferably, greater than 80% water.

The composition according to the invention is stable, i.e., it does not separate or demix at room temperature for at least 2 months.

The elastomeric polyorganosiloxanes in accordance with the invention are partially or totally crosslinked and of three-dimensional structure. When included in an organic phase, they become converted, depending on the content of oily phase used, from a product of spongy appearance when they are used in the presence of small amounts of oily phase, into a homogeneous gel, in the presence of larger amounts of oily phase. The gelation of the oily phase by these elastomers may be total or partial. The terms partially and totally crosslinked are understood by one of ordinary skill in the art, and may include 10%, 20%, 30%, 40%, 50%, 60%, 70%, 80%, and 90% crosslinked, substantially totally crosslinked, and totally crosslinked, and any subrange or value of crosslinking therebetween. The determination of degree of crosslinking is well-known to one of ordinary skill in the elastomeric polyorganosiloxane arts. The above terms and discussion also apply to gelation of the oily phase.

The elastomers of the invention are in the form of a powder or an emulsified gel containing an elastomeric polyorganosiloxane of three-dimensional structure dispersed in a liquid fatty phase.

The expression "liquid fatty phase", also referred to as the "oily phase", means any non-aqueous substance or mixture of non-aqueous substances, which is liquid at room temperature (25° C.) and atmospheric pressure (760 mmHg).

The liquid fatty phase or oily phase can represent from 1 to 80% of the total weight of the composition, preferably from 1 to 50% and better still from 1 to 30%.

The elastomeric polyorganosiloxanes according to the invention can be chosen from the crosslinked polymers obtained by addition reaction and crosslinking reaction in non-aqueous medium, in the presence of a catalyst preferably of platinum type, of at least:

(a) a first polyorganosiloxane (i) containing at least two vinyl groups in the α-ω position on the silicone chain; and (b) a second polyorganosiloxane (ii) containing at least one hydrogen atom linked to one silicon atom per molecule and at least one oxyalkylene group, preferably an oxyethylenated group.

Preferably, the polyorganosiloxane (i) is chosen from polydimethylsiloxanes (PDMS's) and is more preferably an α-ω-dimethylvinyl polydimethylsiloxane. Most preferably, the polyorganosiloxane (ii) is chosen in particular from polydimethylsiloxanes containing one or more hydrogen atom(s), each linked to a silicon atom, and one or more oxyethylenated groups and optionally one or more oxypropylenated groups, linked to a silicon atom via an alkylene radical containing from 1 to 22 carbon atoms.

Optionally, the silicone chains of the first and second polyorganosiloxanes (i) and (ii) contain $C_1$ to $C_6$ alkyl pendent chains and/or aryl chains.

The elastomeric polyorganosiloxanes in the composition according to the invention are preferably in the form of anhydrous gel. This gel can be obtained in particular as follows:

(a) mixing the first polyorganosiloxane (i) and the second polyorganosiloxane (ii);

(b) adding the oily phase to the mixture from step (a); and (c) polymerizing the first polyorganosiloxane (i) and the second polyorganosiloxane (ii) in an oily phase in the presence of a platinum catalyst.

Preferably, the terms, platinum and platinum type refer to catalysts suitable for polymerizing and/or crosslinking polyorganosilanes generally known to those of ordinary skill in the art; and they may include any catalyst containing any of the metals or metallic ions of the platinum group or the platinum metals.

Preferably, the oily phase used in the manufacture of the anhydrous gel contains one or more oils that are liquid at room temperature (25° C.), chosen from hydrocarbon-based oils and/or silicone oils. Preferably, the oily phase is a silicone liquid phase containing one or more oils chosen from PDMS's containing a linear or cyclic chain, which are liquid at room temperature, optionally containing an alkyl or aryl chain pendent or at the chain end, the alkyl chain containing from 1 to 6 carbon atoms.

The expression "hydrocarbon-based oils" means oils mainly containing carbon atoms and hydrogen atoms and in particular alkyl or alkenyl chains, such as alkanes and alkenes. The oils may additionally contain one or more ester, ether, hydroxyl, carboxylic groups and mixtures thereof.

The polyorganosiloxanes of the invention are preferably obtained according to the procedure of Examples 3, 4 and 8 of U.S. Pat. No. 5,412,004 and the examples of U.S. Pat. No. 5,811,487. Preferably, the polyorganosiloxane of Example 3 of U.S. Pat. No. 5,412,004 is used.

The product of Example 3 of U.S. Pat. No. 5,412,004 is in the form of a pasty gel containing about 33% by weight of crosslinked polyorganosiloxane containing (an) oxyethylenated group(s) and about 67% of 6 cSt PDMS. The polyorganosiloxane contains about 18% ethylene oxide relative to the total weight of the polymer.

Preferably, the elastomeric gel of the invention has plastic shear-thinning behaviour with a dynamic viscosity, at low shear in the region of $10^{-3}$ $s^{-1}$–$10^{-4}$ $s^{-1}$, ranging from $2 \cdot 10^6$ P to $4 \cdot 10^6$ P, and a dynamic viscosity ranging from 15 to 50 P for a shear rate of 200 $s^{-1}$, measured with an RS 75 controlled stress rheometer (Haake) at 25° C. in cone/plate geometry; characteristics of the cone: diameter of 20 mm, angle of 1° and gap of 40 $\mu$m. The polyorganosiloxane of the invention also preferably has viscoelastic behaviour at 1 Hz, with a dominant elastic nature at low shear stress values defined as follows: 800 Pa<$G^*_{plateau}$<2500 Pa with $\delta_{plateau}$ in the region of 10°, $G^*_{plateau}$ representing the consistency and $\delta_{plateau}$ representing the elasticity. Preferably, it has a flash point of about 160 to 170° C. at atmospheric pressure. The dynamic viscosity of the elastomeric gel of Example 3 of U.S. Pat. No. 5,412,004 is 45 P for a shear rate of $200^{s-1}$.

Preferably, this elastomeric polyorganosiloxane gel is present in the composition at a content of from 0.5 to 99% and better still from 3 to 75%, which corresponds to an active material content in the polymer of from 0.1 to 33% by weight and better still from 1 to 25%.

Preferably, the elastomeric gel of the invention is, in addition, stable at room temperature for at least 4 months, without any oil exsudation.

Preferably, the particles of elastomeric polyorganosiloxane (as active material) range from 0,1 to 500 $\mu$m and better still from 3 to 200 $\mu$m and most preferably from 3 to 50 $\mu$m in size. These particles can be spherical, flat or amorphous, preferably with a spherical shape.

The elastomeric polyorganosiloxane of the invention is preferably a surfactant with an HLB (hydrophilic-lipophilic balance) of about 2.5. It is thus perfectly suited to the manufacture of a stable water-in-oil emulsion and of a stable oil-in-water-in-oil or water-in-oil-in-water emulsion.

The elastomeric polyorganosiloxane gel can be combined with fatty substances that are liquid at room temperature, waxes or gums that are solid at room temperature, pasty fatty substances of animal, plant, mineral or synthetic origin, and mixtures thereof.

The additional fatty phase can be of any type and can contain products that are liquid at room temperature, such as silicone oils, fluoro oils, fluorosilicone oils or hydrocarbon-based oils which may be partially silicone-containing. These oils may be volatile at room temperature and atmospheric pressure. The expression "volatile oil" in particular means an oil capable of evaporating in less than one hour on contact with the skin or the lips and preferably having a non-zero vapor pressure, in particular ranging from $10^{-3}$ to 300 mmHg (at room temperature and atmospheric pressure) and most preferably greater than 0.3 mmHg.

These oils can represent from 1 to 80% of the total weight of the composition, preferably from 1 to 50% and better still from 1 to 30%.

As preferable oils which can be used in the composition of the invention, mention may be made of:

hydrocarbon-based oils of animal origin, such as perhydrosqualene;

hydrocarbon-based plant oils such as liquid triglycerides of fatty acids, for example sunflower oil, corn oil, soybean oil, marrow oil, grape pip oil, sesame oil, hazelnut oil, apricot oil, macadamia oil, castor oil, avocado oil, caprylic/capric acid triglycerides such as those sold by the company Stearineries Dubois or those sold under the names Miglyol 810, 812 and 818 by the company Dynamit Nobel;

oils of formula $R^1COOR^2$ in which $R^1$ represents a higher fatty acid residue containing from 7 to 19 carbon atoms and $R^2$ represents a branched hydrocarbon-based chain containing from 3 to 20 carbon atoms, such as, for example, purcellin oil, isopropyl myristate or octanoates, decanoates or ricinoleates of alcohols or of polyalcohols, linear or branched hydrocarbons of mineral or synthetic origin, such as volatile or non-volatile liquid paraffins and derivatives thereof, petroleum jelly, polydecenes and hydrogenated polyisobutene such as parleam;

synthetic ethers of formula $R^3COR^4$ in which $R^3$ is a $C_3$ to $C_{19}$ alkyl radical and $R^4$ is a $C_3$ to $C_{20}$ alkyl radical, fatty alcohols such as octyldodecanol or oleyl alcohol;

partially hydrocarbon-based and/or silicone-containing fluoro oils, such as perfluoropolyesters;

silicone oils such as polymethylsiloxanes containing a linear or cyclic silicone chain, which are liquid or pasty at room temperature, phenyl dimethicones, phenyl trimethicones and polymethylphenylsiloxanes, and alkylpolydimethylsiloxanes with a $C_2$ to $C_{20}$ alkyl chain, and mixtures thereof.

The polyorganosiloxane gel containing (an) oxyethylenated group(s) makes it possible to structure these oils in the form of an original "flan" type texture, free of oily gelling agent which would hinder the soft/silky and pleasant feel of the composition.

Preferably, the composition according to the invention can contain at least one wax chosen from hydrocarbon-based waxes, fluoro waxes, silicone waxes and mixtures thereof, which may be solid or semi-solid (in the form of a paste) at room temperature. These waxes can be of plant, mineral, animal and/or synthetic origin. In particular, these waxes have a starting melting point of greater than 25° C. and better still greater than 45° C., at atmospheric pressure. Mixtures of these waxes may also be used.

According to the invention, a wax is a lipophilic fatty substance, which is solid at room temperature, which undergoes reversible solid/liquid changes of state, has a starting melting point which can be up to 200° C. and has an anisotropic crystal organization in the solid state. By bringing the wax to its melting point, it is possible to make it miscible with the liquid fatty phase and to form a microscopically homogeneous mixture, and then by returning the temperature of the mixture to room temperature, crystallization of the wax in the liquid fatty phase of the mixture is obtained.

The preferred silicone waxes can be waxes containing a silicone structure and units containing one or more alkyl or alkoxy chains pendent and/or at the end, of silicone structure, these chains being linear or branched and containing from 10 to 45 carbon atoms. These waxes are referred to, respectively, as alkyl dimethicones and alkoxy dimethicones. Moreover, these alkyl chains can contain one or more ester functions.

As other preferred waxes which can be used in the invention, mention may be made of waxes of animal origin such as lanolin or beeswax; waxes of plant origin such as carnauba wax or candelilla wax; waxes of mineral origin, for example paraffin wax, lignite wax or microcrystalline waxes, ceresin or ozokerite; synthetic waxes such as polyethylene waxes.

These fatty substances can be chosen in a varied manner by a person skilled in the art in order to prepare a composition having the desired properties, for example in terms of consistency or texture.

In particular, the presence of waxes makes it possible to ensure good mechanical strength, preferably when the composition is in the form of a stick.

In general, the composition can contain from 0 to 50% of wax relative to the total weight of the composition, and preferably from 5 to 30%.

The composition of the invention preferably contains a liquid aqueous phase, and in particular one containing water and water-miscible solvents in any proportion, such as polyols (glycerol, diglycerol, ethylene glycol), $C_2$ to $C_5$ lower monoalcohols, acetone and diacetone. Mixtures of these are possible. The aqueous phase can represent from 0 to 75% of the total weight of-the composition, more preferably from 2 to 60% and better still from 5 to 50%.

The composition of the invention can also contain any additive usually used in the field concerned, such as water-soluble or liposoluble dyes, antioxidants, essential oils, preserving agents, cosmetic or dermatological active agents, liposoluble polymers, in particular hydrocarbon-based liposoluble polymers such as polyalkylenes, aqueous-phase gelling agents, fatty-phase gelling agents, fragrances and electrolytes such as monovalent or divalent inorganic salts (NaCl, $MgCl_2$, $MgSO_4$). Mixtures of these are possible.

These additives can be present in the composition in the amounts usually used and, for example, in a proportion of from 0 to 20% of the total weight of the composition, and better still from 0.1 to 10%. Specifically at least 30 to 60 millimoles are used for the electrolytes.

Preferably, the composition of the invention contains one or more aqueous-phase gelling agents as additives, i.e. compounds capable of giving the composition a gelled appearance and of thickening it. Among the preferred aqueous-phase gelling agents which can be used according to the invention, mention may be made of: water-soluble cellulosic gelling agents such as hydroxyethylcellulose, methylcellulose, hydroxypropylcellulose, carboxyethylcellulose and carboxylmethylcellulose; guar gum; quaternized guar gum; nonionic guar gums containing $C_1$–$C_6$ hydroxyalkyl groups; xanthan gum, carob gum, scleroglucan gum, gellan gum, rhamsan gum or karaya gum; alginates, maltodextrin, starch and its derivatives, hyaluronic acid and its salts; clays and in particular montmorillonites, hectorites, bentones or laponites; polymers containing a carboxylic group, for instance crosslinked polyacrylic acids which are at least partially neutralized, such as the "Carbopol" or "Carbomer" products from the company Goodrich (Carbomer 980, for example, neutralized with triethanolamine—abbreviated as TEA); polyglyceryl (meth) acrylate polymers; polyvinylpyrrolidone; polyvinyl alcohols; crosslinked acrylamide polymers and copolymers; crosslinked methacryloyloxyethyltrimethylammonium chloride homopolymers; associative polyurethanes. Mixtures of these are possible.

According to the invention, the aqueous-phase gelling agent is preferably chosen from xanthan gum, clays (bentone or laponite), associative polyurethanes, cellulosic thickeners, in particular hydroxyethylcellulose, and crosslinked polyacrylic acids which are at least partially neutralized.

Needless to say, a person skilled in the art will take care to select the optional additional additives and/or the amount thereof such that the advantageous properties of the composition according to the invention are not, or are not substantially, adversely affected by the addition envisaged. In particular, these additives should not harm the homogeneity, stability, comfort, matte-effect, freshness, migration resistance or "transfer resistance" of the composition.

The composition according to the invention can be in the form of a colored product and preferably in the form of a make-up product for the skin, in particular a foundation, a face powder, an eyeshadow, an eyeliner or a concealer stick, a make-up product for the body (tattoo), a make-up product for the superficial body growths, such as a mascara or a nail varnish, or a make-up product for the lips, such as a lipstick. They can also be in uncolored form, optionally containing cosmetic or dermatological active agents. In this case, they can be used as a care base for the lips (lip balms for protecting the lips against the cold and/or sunlight and/or the wind) or a fixing base to be applied to a conventional lipstick (the fixing base in this case forming a protective film over the film of lipstick, which limits its transfer).

The composition of the invention can also be in the form of a dermatological or cosmetic composition for treating or caring for the skin (including the scalp), keratin fibres (hair, eyelashes, eyebrows), the nails, or the lips, or in the form of an antisun composition or an artificial tanning composition, or alternatively in the form of a cleansing or make-up-removing product for the skin or keratin fibres, or a deodorant product.

Needles to say, the composition of the invention should be cosmetically or dermatologically acceptable, i.e. non-toxic and capable of being applied to human skin (including the inside of the eyelids) or lips. For the purposes of the invention, the expression "cosmetically acceptable" means having a pleasant appearance, odor and feel.

Preferably, the composition of the invention can contain a particulate phase, which is generally present in a proportion of from 0 to 60% relative to the total weight of the composition, preferably from 5 to 35%, and which can contain pigments and/or nacres and/or fillers usually used in cosmetic compositions.

The term "pigments" should be understood as meaning white or colored, inorganic or organic particles, which are soluble in the medium of the composition, and are intended to color and/or opacify the composition. The term "fillers" should be understood as meaning colorless or white, inorganic or synthetic, lamellar or nonlamellar particles. The term "nacres" should be understood as meaning iridescent particles, produced in particular by certain molluscs in their shell, or else synthesized. These fillers and nacres serve to modify the texture of the composition as well as the matte/sheen effect.

The pigments can be present in the composition in a proportion of from 0 to 60% relative to the weight of the final composition, and preferably in a proportion of from 4 to 25%. As inorganic pigments which can be used in the invention, mention may be made of titanium oxide, zirconium oxide or serum oxide, as well as zinc oxide, iron oxide or chromium oxide and ferric blue. Among the organic pigments which can be used in the invention, mention may be made of carbon black and barium, strontium, calcium and aluminium lakes. The pigments can be coated or uncoated.

The nacres can be present in the composition in a proportion of from 0 to 20% relative to the total weight of the composition, preferably at a level of about 2 to 15%. Among the nacres which can be used in the invention, mention may be made of mica coated with titanium oxide, with iron oxide, with natural pigment or with bismuth oxychloride, such as colored titanium mica.

The fillers can be present in a proportion of from 0 to 35% relative to the total weight of the composition, preferably 0 to 15%. Mention may be made in particular of talc, mica, silica, kaolin, Nylon (in particular Orgasol) powder and polyethylene powder, Teflon, starch, boron nitride, copolymer microspheres such as Expancel (Nobel Industrie), Polytrap (Dow Corning) and silicone resin microbeads (for example Tospearl from Toshiba) and fibres, for example polyamides.

Preferably, the composition is free of absorbent fillers such as talc, silica, kaolin or Nylon powders. On the other hand, it can contain non-absorbent fillers which have light-scattering optical properties.

The polyorganosiloxane containing (an) oxyethylenated group(s) has the advantage of dispersing the pigments well and of thus imparting a uniform make-up effect. It also has the advantage of appreciably stabilizing the compositions, in particular when they are in emulsion form.

The composition according to the invention can be manufactured without heating or by heating one or more elastomeric polyorganosiloxanes in anhydrous gel form, adding one or more pigments and/or one or more other additives, optionally adding molten fatty substances (brought in particular to the highest melting point of the waxes), optionally adding the aqueous phase and then emulsifying, if necessary.

It can also be obtained by extrusion as described in application EP-A-667 146. This process includes blending the paste (waxes+oils+water+additives+pigments) while cooling it, to create, in the bulk, zones of crushing of the paste with the aid of a roll mill or a screw extruder-blender. This process produces a composition in the form of a soft paste.

A subject of the invention is also the cosmetic use of particles of a crosslinked elastomeric solid polyorganosiloxane containing at least one oxyalkylene group, in particular an oxyethylene group, in a cosmetic composition or for the manufacture of a treatment or care composition for the skin or the lips in order to increase the matte effect and/or its staying power and/or its resistance to sebum and/or to reduce the transfer and/or the migration of the said composition.

Preferably, the composition is free of silicone resin, so as to conserve the comfortable-feel properties when it is applied and over time.

A subject of the invention is also a cosmetic process for increasing the provision of a matte effect and/or the staying power and/or the resistance to sebum and/or for reducing the transfer and/or the migration of a cosmetic composition, which consists in introducing into the composition particles of crosslinked elastomeric polyorganosiloxane as defined above.

Preferably, the invention relates to a matte-effect composition containing a liquid fatty phase and, as lipophilic surfactant and thickener for the said fatty phase, particles of a crosslinked elastomeric solid polyorganosiloxane containing at least one oxyalkylenated group, in particular-an oxyethylenated group. The invention also preferably relates to the use of these particles of elastomeric solid polyorganosiloxane in a care or make-up composition or for the manufacture of a care or make-up composition to give a matte effect to the skin or the lips and/or to camouflage the imperfections of the skin and/or the lips. This composition is more preferably a lipstick or a foundation for making up both the human face and the human body. This composition is soft and feels fresh when applied, its spreads easily, is non-sticky and it does not dry out the skin or the lips. Despite the presence of fatty substances, the composition is entirely suitable for greasy skin, on account of its high matte-effect power.

EXAMPLES

Having generally described this invention, a further understanding can be obtained by reference to certain specific examples, which are provided herein for purposes of illustration only and are not intended to be limiting unless otherwise specified. The percentages are given on a weight basis.

Example 1

Preparation of a Matte Foundation with a "Custard" Texture

| | |
|---|---|
| Fatty phase | |
| Silicone oil (PDMS, 6 cSt) | 10% |
| Pigment | 10% |
| Modified silicone | |
| (Example 3 of U.S. Pat. No. 5,412,004) | 18% (5.7% active material) |
| Aqueous phase | |
| Preserving agent | qs |
| Divalent salt | 0.4% |
| Water | qs 100% |

Result:

Production of a foundation with a gel texture of "custard" (dessert) type, which gives a very strong matte effect, has a very fresh sensation when applied, has good staying power over time and conserves the matte effect over time, unlike the products of the prior art. The foundation also has transfer-resistance and migration-resistance properties.

Preparation:

The polyorganosiloxane is swollen in the oil at room temperature, followed by addition of the pigments and aqueous phase, and the whole is then mixed together with stirring until the oily phase has emulsified in the aqueous phase.

Example 2

Preparation of a Matte-effect Care Cream

| Fatty phase | |
| --- | --- |
| Modified silicone (example 3 of U.S. Pat. No. 5,412,004) | 18% |
| Silicone Oil (PDMS, 6 cSt) | 10% |
| Aqueous phase | |
| Preserving agent | qs |
| Divalent salt | 0.7% |
| Water | qs 100% |

Result:

Preparation of a non-greasy cream the consistency of "dessert" type, as a Jello® or a custard which feels fresh, gives a very strong matte effect and has good staying power over time. This cream contains more than 70% of water, without adding any surfactant other than the elastomer, or any co-emulsifier.

Preparation:

This composition is prepared as in Example 1.

The cream was tested in comparison with a cream of the prior art based on KSG 6 and another based on KSG 21. It was judged to give a very strong matte effect, whereas the other creams of the prior art were judged to be shiny. In addition, its transfer-resistance and migration-resistance properties are greater than those of KSG 6.

Comparative Test

A commercial product, Eclamat of Phas without elastomeric organopolysiloxane and considered by a person skilled in the art like a cosmetician as a mattifying product was compared to a composition according to the invention.

This comparative test was carried out on 28 women with greasy and shiny skin on the forehead on half the face (a treated region of the forehead in contrast to an untreated region). The shininess of the skin was measured using a device of the Matidiag SEI-M-0029-MAT101 type, as disclosed in French application FR-A-2,650,890, the disclosure of which is incorporated herein by reference. The measurements were made at time T0, T10 minutes, T1 hour and T3 hours.

| Treatments | T15 minutes - T0 | T1 hour - T0 | T2 hours - T0 | T6 hours - T0 |
| --- | --- | --- | --- | --- |
| Invention | −18% | −16% | −13% | −10% |
| Eclamat | −7% | −5% | −4% | −4% |

It is clear from this table that the hydrophillic organopolysiloxane conferred a matte appearance, which was significantly better than that of the lipophillic organopolysiloxane. This superiority was even apparent to a significant extent to the naked eye. This was because the product had a greater mattifying effect as the measured value became more negative. In addition, this matteness exhibited good hold over time.

The entire contents of each of the references, applications, and patents recited hereinabove is hereby incorporated by reference.

This application is based on French application FR 99 03967, filed Mar. 30, 1999, the entire contents of which is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. A dermatologic or cosmetic composition, comprising:
   a liquid fatty phase, and
   as surfactant and thickener for said liquid fatty phase, particles of a crosslinked elastomeric solid polyorganosiloxane comprising at least one oxyalkylenated group.

2. The composition according to claim 1, wherein the oxyalkylenated group comprises at least one oxyethylene group.

3. The composition according to claim 1, wherein the elastomeric solid polyorganosiloxane comprises only oxyethylenated groups as oxyalkylenated groups.

4. The composition according to claim 1, wherein the elastomeric solid polyorganosiloxane is obtained by addition reaction and crosslinking reaction in non-aqueous medium, in the presence of a platinum type catalyst, of at least:
   a first polyorganosiloxane (i) containing at least two vinyl groups in the α-ω position on the silicone chain per molecule; and
   a second polyorganosiloxane (ii) containing at least one hydrogen atom linked to one silicon atom per molecule and at least one oxyalkylene group.

5. The composition according to claim 4, wherein the first polyorganosiloxane (i) comprises at least one polydimethylsiloxane.

6. The composition according to claim 4, wherein the first polyorganosiloxane (i) is an α-ω-dimethylvinyl polydimethylsiloxane.

7. The composition according to claim 4, wherein the second polyorganosiloxane (ii) comprises at least one polydimethylsiloxane comprising one or more hydrogen atoms and one or more oxyalkylenated groups linked to a silicon atom via an alkylene radical containing from 1 to 22 carbon atoms.

8. The composition according to claim 1, wherein said particles are in the form of an anhydrous gel obtained according to a method comprising:
   (a) mixing first and second polyorganosiloxanes (i) and (ii); said first polyorganosiloxane (i) containing at least two vinyl groups in the α-ω position on the silicone chain per molecule; and said second polyorganosiloxane (ii) containing at least one hydrogen atom linked to one silicon atom per molecule and at least one oxyalkylene group;
   to obtain a mixture; and
   (b) adding a liquid fatty phase to the mixture from step (a);
   (c) polymerizing the first and second polyorganosiloxanes (i) and (ii) in the liquid fatty phase in the presence of a platinum type catalyst.

9. The composition according to claim 1, wherein the particles are in the form of a gel, said gel having:
   a viscoelastic behavior of 1 Hz;
   a shear stress of 800 Pa<$G^*_{plateau}$<2500 Pa; and
   a $\delta_{plateau}$ in the region of 10°;
   wherein $G^*_{plateau}$ is the consistency and wherein $\delta_{plateau}$ is the elasticity.

10. The composition according to claim 1, wherein the particles have a size form 3 to 200 μm.

11. The composition according to claim 1, wherein the liquid fatty phase comprises at least one oil selected from the group consisting of a hydrocarbon-based oil, a silicone liquid oil, and a mixture thereof.

12. The composition according to claim 1, further comprising at least one fatty substance selected from the group consisting of volatile or non-volatile oils, waxes, gums and pasty fatty substances, of animal, plant, mineral or synthetic origin, and mixtures thereof.

13. The composition according to claim 1, wherein the elastomeric solid polyorganosiloxane represents from 0.1 to 33% by weight, relative to the total weight of the composition.

14. The composition according to claim 1, further comprising an aqueous phase in an amount of from 0 to 75% relative to the total weight of the composition.

15. The composition according to claim 1, wherein the liquid fatty phase represents from 1 to 80% relative to the total weight of the composition.

16. The composition according to claim 1, further comprising a particulate phase in a proportion of 0 to 60% relative to the total weight of the composition.

17. The composition according to claim 1, further comprising at least one cosmetic or dermatological active agent.

18. The composition according to claim 1, wherein the composition is free of absorbent filler and/or of surfactant other than the elastomeric polyorganosiloxane.

19. The composition according to claim 1, wherein the composition is in the form of a foundation, face powder or eyeshadow composition, a concealer product, a lipstick, an eyeliner, a mascara, a nail varnish, a make-up product for the body, a care base or fixing base for the lips, a dermatological product or care product for the skin or keratin fibres, an antisun composition or artificial tanning composition, a cleansing product for the skin or keratin fibres, or a deodorant product.

20. The composition according to claim 1, further comprising at least one ingredient selected from the group consisting of preserving agents, fragrances, aqueous-phase gelling agents, electrolytes, and mixtures thereof.

21. The composition according to claim 20, wherein the elastomeric solid polyorganosiloxane is obtained by addition reaction and crosslinking reaction in non-aqueous medium, in the presence of a platinum type catalyst, of at least:
   a first polyorganosiloxane (i) containing at least two vinyl groups in the α-ω position on the silicone chain per molecule; and
   a second polyorganosiloxane (ii) containing at least one hydrogen atom linked to one silicon atom per molecule and at least one oxyalkylene group.

22. The composition according to claim 20, wherein said particles are in the form of an anhydrous gel obtained according to a method comprising:
   (a) mixing first and second polyorganosiloxanes (i) and (ii); said first polyorganosiloxane (i) containing at least two vinyl groups in the α-ω position on the silicone chain per molecule; and said second polyorganosiloxane (ii) containing at least one hydrogen atom linked to one silicon atom per molecule and at least one oxyalkylene group;
   to obtain a mixture; and
   (b) adding a liquid fatty phase to the mixture from step (a);
   (c) polymerizing the first and second polyorganosiloxanes (i) and (ii) in the liquid fatty phase in the presence of a platinum type catalyst.

23. The composition according to claim 14, wherein the aqueous phase constitutes at least 60% by weight relative to the total weight of the composition.

24. The composition according to claim 14, wherein the aqueous phase constitutes at least 70% by weight relative to the total weight of the composition.

25. The composition according to claim 14, wherein the aqueous phase constitutes at least 80% by weight relative to the total weight of the composition.

26. The composition according to claim 19, wherein the composition is in the form of a lipstick.

27. The composition according to claim 26, wherein the lipstick is transfer-resistant.

28. The composition according to claim 26, wherein the lipstick is migration-resistant.

29. The composition according to claim 27, wherein the lipstick is migration-resistant.

30. The composition according to claim 19, wherein the composition is in the form of a fixing base to be applied to a conventional lipstick.

31. The composition according to claim 19, wherein the composition is in the form of a foundation.

32. The composition according to claim 31, wherein the foundation is transfer-resistant.

33. The composition according to claim 31, wherein the foundation is migration-resistant.

34. The composition according to claim 32, wherein the foundation is migration-resistant.

35. The composition according to claim 1, further comprising at least one filler.

36. The composition according to claim 1, further comprising at least one pigment.

37. The composition according to claim 35, further comprising at least one pigment.

38. The lipstick according to claim 26, further comprising at least one filler.

39. The lipstick according to claim 26, further comprising at least one pigment.

40. The lipstick according to claim 38, further comprising at least one pigment.

41. The foundation according to claim 31, further comprising at least one filler.

42. The foundation according to claim 31, further comprising at least one pigment.

43. The foundation according to claim 41, further comprising at least one pigment.

* * * * *

UNITED STATES PATENT AND TRADEMARK OFFICE
CERTIFICATE OF CORRECTION

PATENT NO. : 6,548,050 B1
DATED : April 15, 2003
INVENTOR(S) : Isabelle Bara

It is certified that error appears in the above-identified patent and that said Letters Patent is hereby corrected as shown below:

<u>Column 14,</u>
Line 65, "3to" should read -- 3 to --.

Signed and Sealed this

Fifteenth Day of July, 2003

JAMES E. ROGAN
*Director of the United States Patent and Trademark Office*